Figure 1:
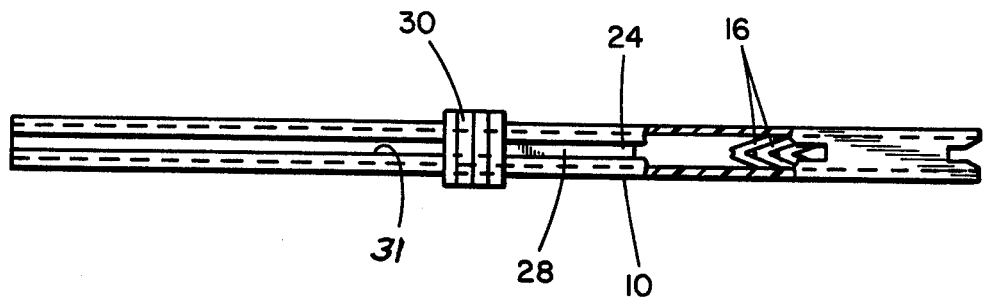

United States Patent [19]

Samuels et al.

[11] 4,108,306
[45] Aug. 22, 1978

[54] CARTRIDGE FOR SUTURE CLIPS

[76] Inventors: Peter B. Samuels, 14708 Sutton St., Sherman Oaks, Calif. 91403; Ernest C. Wood, 2461 Ivanhoe Dr., Los Angeles, Calif. 90039

[21] Appl. No.: 807,967

[22] Filed: Jun. 20, 1977

[51] Int. Cl.² .............................................. B65D 85/20
[52] U.S. Cl. .................................. 206/339; 221/279; 227/121
[58] Field of Search ............................... 206/338–340; 221/232, 279; 227/19, 121, 125–126

[56] References Cited

U.S. PATENT DOCUMENTS

| 3,480,181 | 11/1969 | Bauer | 221/279 |
| 3,775,825 | 12/1973 | Wood et al. | 29/816 X |

FOREIGN PATENT DOCUMENTS 883,860 7/1953 Fed. Rep. of Germany .......... 227/121

*Primary Examiner*—Steven E. Lipman
*Attorney, Agent, or Firm*—McDougall, Hersh & Scott

[57] ABSTRACT

A cartridge for feeding pairs of clips simultaneously in laterally spaced apart relation between a pair of clamping jaws whereby the outermost pair of clips are clamped onto an elongate member such as a vessel, in which the cartridge is formed with a pair of laterally spaced apart slots for holding a plurality of clips and a slide for endwise displacement of the clips within the slots and a spring clip for permitting the slide to move forwardly in feeding relation while resisting backward displacement.

2 Claims, 3 Drawing Figures

CARTRIDGE FOR SUTURE CLIPS

This invention relates to a cartridge in which a plurality of clips are adapted to be housed and fed to a means for clamping the clips onto elongate elements, such as vessels (suturing clips) threads and the like.

In our earlier issued U.S. Pat. No. 3,775,825, description is made of a clip applicator having a pair of normally spaced apart jaws which are pivottaly mounted on a body portion for rocking movement into engagement with clips, supported therebetween, for clamping a pair of clips simultaneously onto closely spaced apart portions of a thread with cutting means pivoted coaxially on the body portion for movement between the spaced apart jaws for severing the elongate member after the jaws have clamped to secure the spaced apart clips thereon.

Use is made of a cartridge in the form of an elongate member of rectangular shape, having a pair of slots extending continuously therethrough dimensioned to receive a column of clips in each slot.

A slide is provided for displacement through an elongate opening within the rectangular member for engagement with the endmost clip in each of the columns for endwise displacement of the columns to bring the forwardmost clip into position to be engaged by the confronting surface of the clamping jaws. The elongate cartridge is provided with a central passage to enable an exposed handle portion to be connected to the slide for endwise displacement through the housing for corresponding displacement of the columns of clips as the need arises. The end of the elongate housing is provided with a notch to permit passage of the cutting means between the jaws for severing the thread, vessel or the like between the clipped portions.

It has been found on occasion that the columns of clips are subject to backward displacement responsive to the forces applied when the jaws are brought into engagement with the outermost clips in the column for clamping the clips onto the elongate member. Such inadvertent backdisplacement results in misalignment with the jaws and/or less effective engagement with the elongate member whereby optimum clamping engagement is not achieved.

It is an object of this invention to provide a cartridge of the type described embodying an improvement which enables the columns of clips to be freely and easily advanced through the cartridge properly to position the outermost clips in the columns between the clamping jaws, but which prevents backward displacement of the columns whereby the outermost clips are prevented from movement from the desired oriented position between the clamping jaws.

Figure 2:
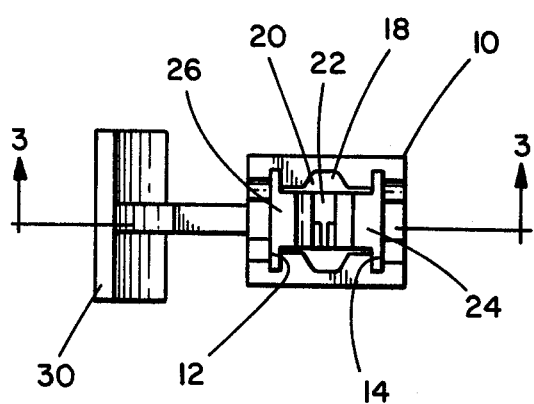
Figure 3:
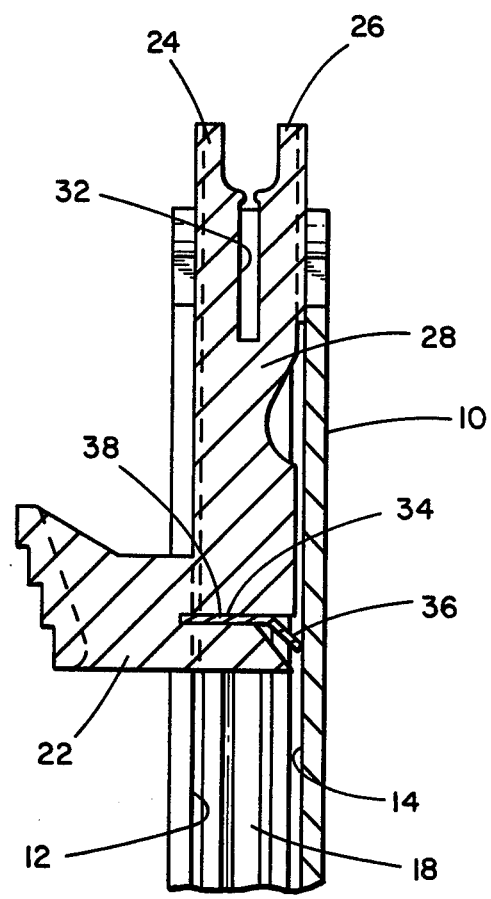

These and other objects and advantages of this invention will hereinafter appear, and for purposes of illustration, but not of limitation, an embodiment of the invention is shown in the accompanying drawing in which:

FIG. 1 is a side elevational view of a cartridge embodying the features of this invention, FIG. 2 is an end elevational view of the cartridge shown in FIG. 1, FIG. 3 is a sectional view taken along the line 3—3 of FIG. 2, showing the slide and the means for automatically blocking backward movement of the slide within the housing.

The cartridge comprises elongate housing 10 of rectangular shape having laterally spaced apart slots 12 and 14 extending continuously therethrough in which clips 16 are retained therein in stacked relation. A passage 18 extending lengthwise through the center of the housing 10, between the slots 12 and 14, and joined thereto by contiguous passage 20, is provided with a slide 22 which is freely displaceable lengthwise through the housing. The slide 22 has a bifurcated end portion, the outer extremity of which, namely 24 and 26, slide in the slots 12 and 14 for engagement with the lowermost clip in each stack. A rib 28 extends inwardly from the bifurcated portions to slide as a guide within the contiguous portions 20 connecting the slides 12 and 14 with the central passage 18.

A handle portion 30 extends through an elongate opening 31 in a wall of the housing and into engagement with the slide 22 to enable displacement thereof in response to external force applied to the handle 30. For this purpose, the handle 30 is inclined from the slide in a forwardly direction so that the force can be applied by a finger of the hand holding the clip applicator into which the cartridge has been inserted. A notch 32 is provided in the end portion of the slide to permit passage of the thread severing means when the last of the clips are being fed from the cartridge.

The means to militate against retrograde movement of the slide 22 with corresponding protection against backward displacement of the clips comprises a slot 34 extending inwardly from the wall opposite the handle 30 and a spring clip 36 having one end portion 38 dimensioned to correspond to the depth of the slot and an outer end portion projecting from the slot at a slight angle in the direction rearwardly with respect to the movement of the slide in feeding relation, and dimensioned to have a length resiliently to engage the adjacent wall of the cartridge. An incline at an angle anywhere within the range of 30° to 80° with the plane of the back wall will be sufficient. Under these conditions, the clip will offer little if any resistence to movement of the slide in the forward direction responsive to forwardly directed force on the handle 30. However, forces to urge the slide in the backward direction will be resisted by the engagement by the end of the angled portion of the clip 36 with the adjacent wall of the housing. Thus the column of clips can be advanced freely to locate the outermost clips in each column in position of use between the clamping jaws while backward movement will be prevented no matter how hard the two outermost clips are pushed by the jaws during clamping and severing.

It will be understood that changes may be made in the details of construction, arrangement and operation, without departing from the spirit of the invention, especially as defined in the following claims.

We claim:

1. A cartridge for feeding pairs of clips simultaneously in laterally spaced apart relation from an elongate housing having a central passage, a pair of slots extending through at least the major portion of the housing with a passage in between for receiving a plurality of clips in each slot aligned in end to end relation, with the slots communicating with the central passage through a contiguous opening of smaller dimension than the slots and passage, a slide within the passage, and arms extending laterally from the slide through the openings into the slots for engagement with the endmost of the clips in the slots, a handle extending from the housing and operatively connected with the slide for endwise displacement through the passage, the improvement in a means to permit the slide to move forwardly while preventing rearward movement in the passage comprising a spring clip having a forward end portion received within a slot extending inwardly from the wall of the slide opposite the handle and a trailing end portion which extends beyond the slide into engagement with the adjacent wall of the housing, with the trailing end portion being angled to extend backwardly to permit forward movement of the slide relative to the housing while preventing relative backward movement, in which the spring clip comprises a flat strip of spring metal in which the forward portion is dimensioned to have a length corresponding to the length of the slot in the slide and a trailing portion in which the total length of the strip is greater than the distance between the base of the slot to the adjacent wall of the housing for resilient engagement between the clip and the wall.

2. A cartridge as claimed in claim 1, in which the trailing end portion of the spring clip extends downwardly at an angle of 30° to 80° with the adjacent wall of the housing.

* * * * *